US007651262B2

United States Patent
Nishina et al.

(10) Patent No.: US 7,651,262 B2
(45) Date of Patent: Jan. 26, 2010

(54) APPARATUS FOR DISCRIMINATING LIQUID REDUCING AGENT

(75) Inventors: Mitsuhiro Nishina, Ageo (JP); Hideki Matsunaga, Ageo (JP)

(73) Assignee: Nissan Diesel Motor Co., Ltd., Ageo-shi (JP)

( * ) Notice: Subject to any disclaimer, the term of this patent is extended or adjusted under 35 U.S.C. 154(b) by 226 days.

(21) Appl. No.: 11/945,201

(22) Filed: Nov. 26, 2007

(65) Prior Publication Data

US 2008/0089384 A1      Apr. 17, 2008

Related U.S. Application Data

(63) Continuation of application No. PCT/JP2006/309599, filed on May 12, 2006.

(30) Foreign Application Priority Data

Oct. 6, 2005    (JP)    ............... 2005-171391

(51) Int. Cl.
- *G01N 25/00* (2006.01)
- *G01K 3/00* (2006.01)
- *G01K 1/00* (2006.01)

(52) U.S. Cl. .................. 374/45; 374/112; 374/144; 374/54; 73/61.76

(58) Field of Classification Search ................. 374/45, 374/112, 144, 54; 73/61.76
See application file for complete search history.

(56) References Cited

U.S. PATENT DOCUMENTS

| 2005/0011183 | A1 | 1/2005 | Ripper et al. | |
| 2007/0054409 | A1* | 3/2007 | Inoue et al. | ................. 436/108 |
| 2007/0163240 | A1 | 7/2007 | Nishina et al. | |
| 2007/0199308 | A1* | 8/2007 | Satou et al. | ................. 60/286 |
| 2007/0209428 | A1 | 9/2007 | Nishina et al. | |
| 2008/0087009 | A1* | 4/2008 | Nishina et al. | ................. 60/301 |
| 2009/0193793 | A1* | 8/2009 | Matsunaga | ................. 60/287 |

FOREIGN PATENT DOCUMENTS

| EP | 1322921 A1 | 9/2001 |
| EP | 1356194 A1 | 1/2002 |
| JP | 2000-027627 | 1/2000 |
| JP | 2005-127262 A | 5/2005 |
| JP | 2005-133541 | 5/2005 |
| WO | WO 02/27280 A2 | 4/2002 |
| WO | WO 02/057603 A1 | 7/2002 |
| WO | WO 2005/040567 A1 | 5/2005 |
| WO | WO 2005/040570 A1 | 5/2005 |

* cited by examiner

*Primary Examiner*—Gail Verbitsky
*Assistant Examiner*—Mirellys Jagan
(74) *Attorney, Agent, or Firm*—McDermott Will & Emery LLP

(57) ABSTRACT

A discriminating apparatus of liquid reducing agent is disclosed, in which, based on concentration of liquid reducing agent which is measured at each predetermined time after starting of engine, discrimination is processed whether the storage tank is filled with dissimilar aqueous solution, the storage tank is normally filled with the liquid reducing agent, or the storage tank is empty. When the empty discrimination or the dissimilar aqueous solution discrimination is performed, it is judged whether or not the discrimination is adequate according to the liquid condition in the storage tank. When the empty or the dissimilar aqueous solution discrimination is adequate, the empty discrimination frequency or the dissimilar aqueous solution discrimination frequency is counted up. When the empty discrimination frequency and the dissimilar aqueous solution discrimination frequency become equal to or larger than the first predetermined frequency, the discrimination is upheld.

10 Claims, 12 Drawing Sheets

APPARATUS FOR DISCRIMINATING LIQUID REDUCING AGENT

This application is a continuation of PCT/JP2006/309599, filed on May 12, 2006.

BACKGROUND OF THE INVENTION

1. Field of the Invention

The present invention generally relates to an apparatus for discriminating a condition of a storage tank for storing a liquid reducing agent suitable for use not exclusively but preferably in exhaust emission purification and in particular, to a technology for discriminating with high precision whether the storage tank is empty, a reducing agent is normally filled in the storage tank or the storage tank stores therein any dissimilar aqueous solution, by utilizing a concentration sensor which indirectly measures the concentration of the liquid reducing agent based on heat transfer characteristics between two positions close to each other.

2. Description of the Related Art

As a catalytic purification system for removing nitrogen oxides ($NO_x$) contained in the exhaust emission of an engine, there has been proposed an exhaust emission purifying apparatus disclosed in Japanese Laid-open (Kokai) Patent Application Publication No. 2000-27627. In the exhaust emission purifying apparatus, a reducing agent according to engine operating conditions is injection-supplied to the upstream of the exhaust stream with respect to a reduction catalytic converter, which is disposed in an engine exhaust system, so that $NO_x$ in the exhaust emission and the reducing agent are subjected to the catalytic-reduction reaction to purify $NO_x$ into harmless components.

However, according to the above-described conventional exhaust emission purifying apparatus, when a purification efficiency is changed with a change in concentration of the liquid reducing agent, if a driver continues the operation of the engine without taking notice of this change, the likelihood that the required $NO_x$ purification performance is not successfully exhibited, resulting in an occurrence of an undesirable condition such that a large amount of discharge of $NO_x$ from the engine takes place. In particular, in the case where a storage tank is empty or the dissimilar aqueous solution which does not function as the liquid reducing agent is used, there is caused such an undesirable condition significantly.

Therefore, it may occur to a skilled person in the art to arrange a concentration sensor which indirectly measures the concentration of the liquid reducing agent based on the heat transfer characteristics between two positions close to each other. However, if such a concentration sensor is mounted on a movable vehicle such as an automobile, the following problems might be caused. Namely, during the driving of the movable vehicle, since a vehicle body is continually subjected to vibration due to the irregularity of road surfaces, the convection can be generated in the liquid reducing agent in the storage tank. Further, if the engine coolant or the like is circulated in the storage tank in order to prevent the freezing of the liquid reducing agent, the temperature distribution of the liquid reducing agent might become uneven, resulting in that, similar to the case of vehicle vibration, the convection can be generated in the liquid reducing agent in the storage tank. Then, if the convection is generated in the liquid reducing agent, the heat transfer characteristics using the liquid reducing agent as a heat transfer medium might be changed, and therefore, the measurement accuracy of the concentration of the liquid reducing agent might be significantly lowered.

SUMMARY OF THE INVENTION

Therefore, in view of the problems in the conventional technology as described above, the present invention has an object to provide an apparatus for discriminating liquid reducing agent which is capable of discriminating with high precision whether a storage tank is empty, a liquid reducing agent is normally filled or the liquid in the storage tank is the dissimilar aqueous solution, utilizing a fact that, if the liquid reducing agent is normally filled, it is extremely rare that the concentration of the liquid reducing agent is consecutively deviated in many times from a predetermined range even if the convection is generated in the liquid reducing agent.

Therefore, in accordance with the present invention, one contrivance is taken in which, to a storage tank which stores a liquid reducing agent, there is disposed a concentration sensor incorporating therein temperature sensors arranged at two positions close to each other, and also, a heater incorporated in one of the temperature sensors. A control unit incorporating therein a computer operates the heater of the concentration sensor at each predetermined time after a start of an engine operation to thereby indirectly measure the concentration of the liquid reducing agent based on a temperature detected by each of the temperature sensors, and processes discrimination in a manner such that the storage tank is filled with an aqueous solution dissimilar to the liquid reducing agent when the concentration is lower than a lower threshold, that the storage tank is normally filled with the liquid reducing agent when the concentration is equal to or higher than the lower threshold and also equal to or lower than an upper threshold, and that the storage tank is empty when the concentration is higher than the upper threshold. Further, when it is discriminated that the liquid in the storage tank is the dissimilar aqueous solution, the control unit judges whether or not the dissimilar aqueous solution discrimination is adequate, based on the temperature detected by each of the temperature sensors and the measured concentration, and when it is judged that the dissimilar aqueous solution discrimination is adequate, counts up the frequency of the dissimilar aqueous solution discrimination. Furthermore, when it is discriminated that the storage tank is empty, the control unit judges whether or not the empty discrimination is adequate, based on the temperature detected by each of the temperature sensors, and when it is judged that the empty discrimination is adequate, counts up the frequency of the empty discrimination, and further, when it is discriminated that the liquid reducing agent is normally filled, the control unit resets the frequency of the dissimilar aqueous solution discrimination and the frequency of the empty discrimination. Moreover, the control unit upholds the dissimilar aqueous solution discrimination and the empty discrimination when the frequency of the dissimilar aqueous solution discrimination and the frequency of the empty discrimination become equal to or larger than the first predetermined frequency.

In accordance with the present invention, the apparatus for discriminating liquid reducing agent executes measurement of the concentration of the liquid reducing agent at each predetermined time after the engine operation start, and discrimination is executed in such a manner that the storage tank is filled with any aqueous solution dissimilar to the liquid reducing agent when the concentration is lower than the lower threshold, that storage tank is normally filled with the liquid reducing agent when the concentration is equal to or higher than the lower threshold and also equal to or lower than the upper threshold, and that the storage tank is empty when the concentration is higher than the upper threshold. Further, when it is discriminated that the liquid in the storage tank is the dissimilar aqueous solution, it is judged whether or not the dissimilar aqueous solution discrimination is adequate, and only when the dissimilar aqueous solution discrimination is adequate, the frequency of the dissimilar aqueous solution discrimination is counted up. On the other hand, when it is discriminated that the storage tank is empty, it is judged whether or not the empty discrimination is adequate, and only when the empty discrimination is adequate, the frequency of the empty discrimination is counted up. Then, when the frequency of the dissimilar aqueous solution discrimination and the frequency of the empty discrimination become equal to or larger than the first predetermined frequency, the dissimilar aqueous solution discrimination and the empty discrimination are respectively upheld. Therefore, since the counting is not performed in a state where the liquid type discrimination precision is low, it is possible to discriminate with high precision whether the storage tank is empty, the liquid reducing agent is normally filled or the liquid in the storage tank is the dissimilar aqueous solution, irrespectively of vehicle operating states.

DESCRIPTION OF THE PREFERRED EMBODIMENTS

Details of the present invention will be described hereunder, referring to the accompanying drawings.

Figure 1:
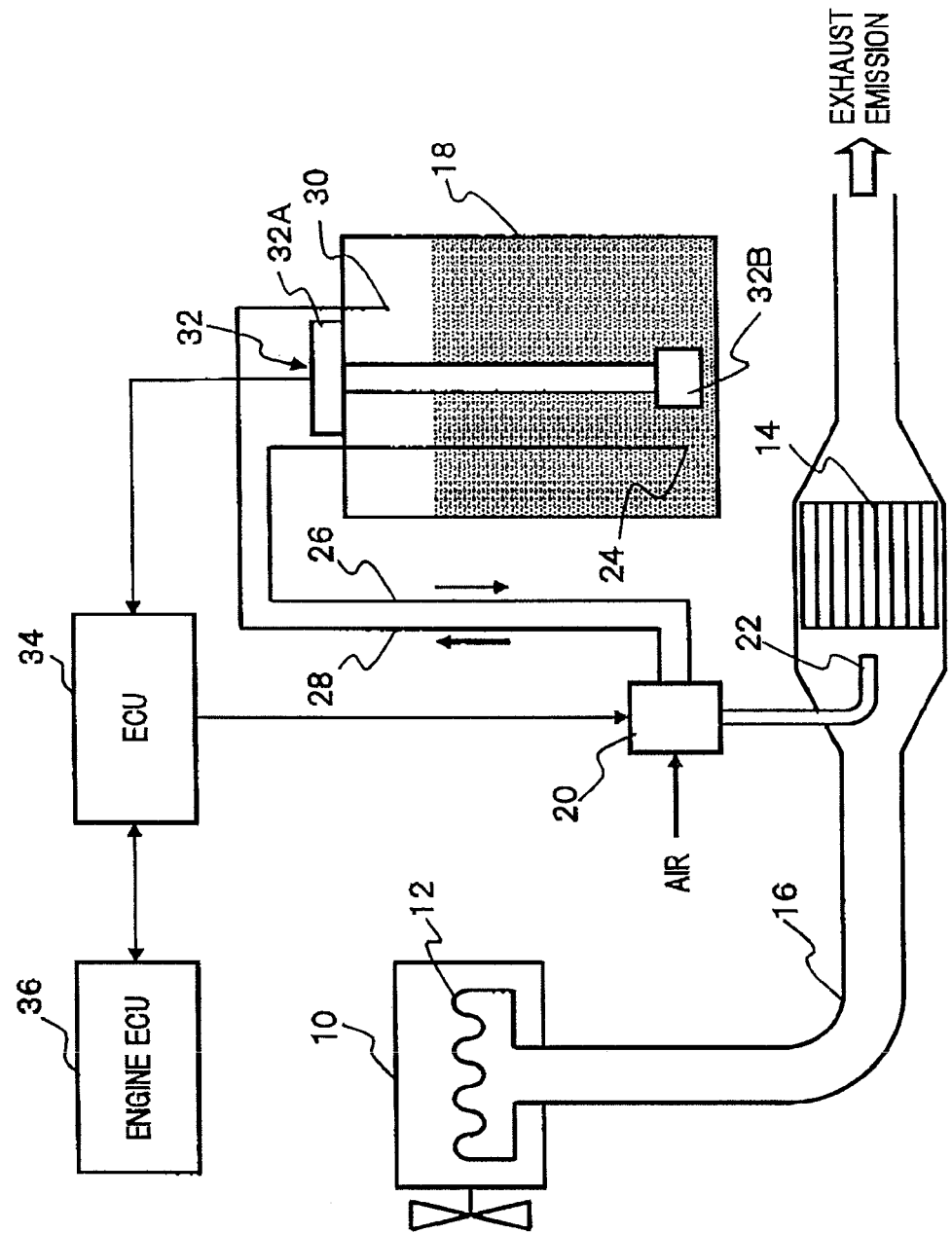
FIG. 1 is an entire block diagram of an exhaust emission purifying apparatus provided with an apparatus for discriminating liquid reducing agent, according to an embodiment of the present invention.

FIG. 1 shows an entire configuration of an exhaust emission purifying apparatus provided with an apparatus for discriminating liquid reducing agent according to the present invention.

The exhaust emission of an engine 10 is discharged into the atmosphere from an exhaust manifold 12 via an exhaust pipe 16 in which a $NO_x$ reduction catalytic converter 14 is disposed. To be specific, in the exhaust pipe 16, there are disposed three catalytic converters, namely, a nitrogen monoxide (NO) oxidation catalytic converter, a $NO_x$ reduction catalytic converter 14 and an ammonia slip oxidation catalytic converter, in this order from the exhaust upstream side, and sensors, such as a temperature sensor, an oxygen sensor and the like, are disposed on the exhaust upstream and downstream of the three catalytic converters, so that an exhaust system is configured, but the details thereof is not shown in the figure. Further, to the exhaust upstream of the $NO_x$ reduction catalytic converter 14, a liquid reducing agent stored in a storage tank 18 passes through a reducing agent supply device 20 and an injection nozzle 22, and is injection-supplied together with the air. Here, as the liquid reducing agent, a urea aqueous solution is used in the present embodiment. However, an ammonia aqueous solution, or diesel oil, petroleum or gasoline, mainly containing hydrocarbon, may be used according to the specification of the $NO_x$ reduction catalytic converter 14.

The urea aqueous solution which is the aqueous solution in which urea in a solid or powder state is dissolved, is sucked via an inlet port 24 which is opened at a lower position in the vicinity of a bottom portion of the storage tank 18, and supplied to the reducing agent supply device 20 through supply piping 26. Here, in the urea aqueous solution supplied to the reducing agent supply device 20, the surplus urea aqueous solution which does not contribute to the injection passes through return piping 28 and is returned into the storage tank 18 via a return port 30 which is opened at an upper position of the storage tank 18.

The urea aqueous solution injection-supplied to the exhaust upstream of the $NO_x$ reduction catalytic converter 14 is hydrolyzed with the exhaust heat and the water vapor in the exhaust emission, so that ammonia is easily generated. It is known that generated ammonia reacts with $NO_x$ in the exhaust emission in the $NO_x$ reduction catalytic converter 14, so as to purify $NO_x$ into the water and the harmless gas.

Further, a concentration sensor 32 outputting a signal relating to the concentration of the urea aqueous solution is attached to the storage tank 18. Namely, a base portion 32A incorporating therein a circuit substrate is fixed on a top wall of the storage tank 18, and also, a detecting portion 32B is suspended from the base portion 32A toward the bottom portion of the storage tank 18.

Figure 2:
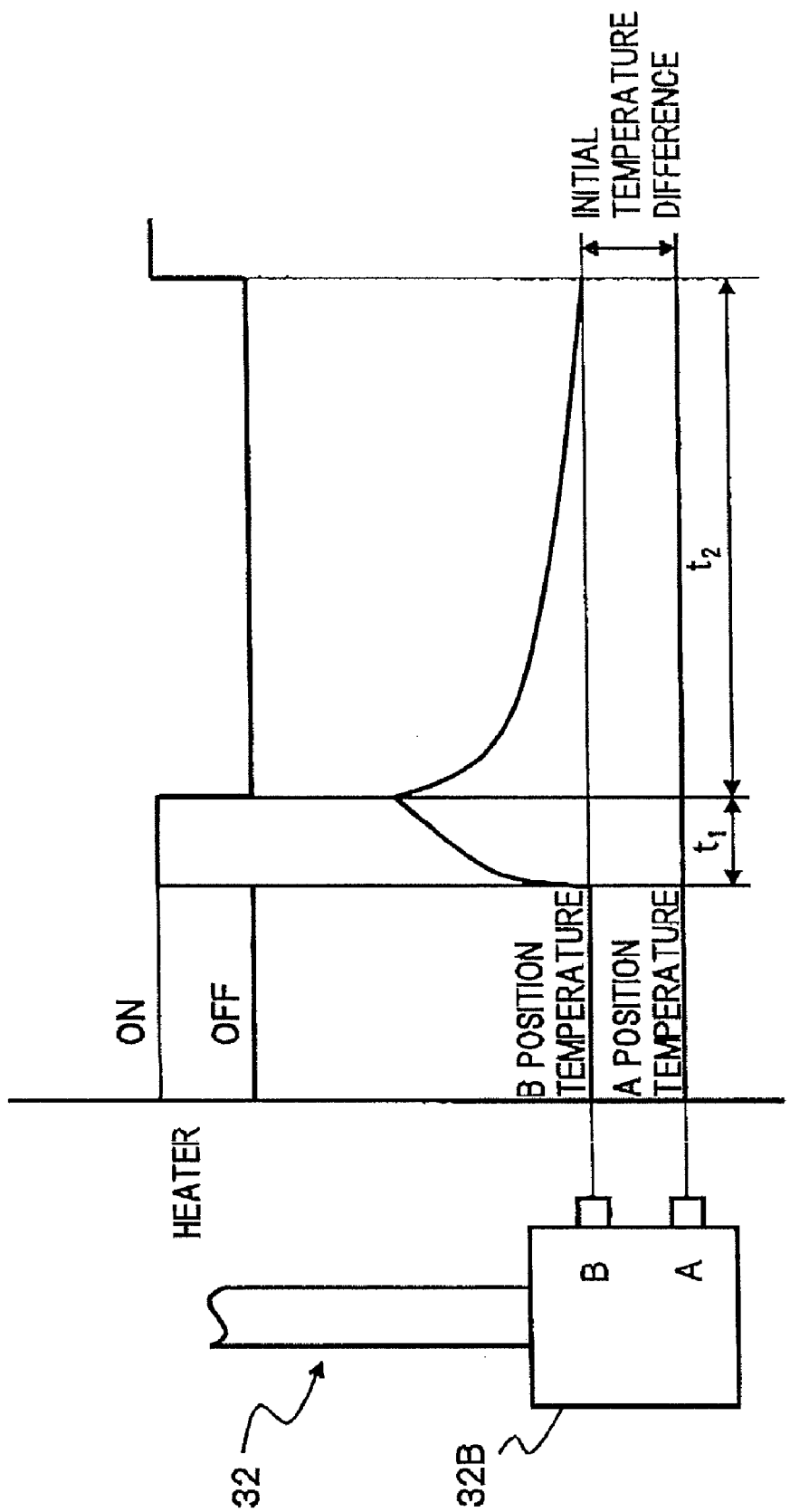
FIG. 2 is an explanatory diagram of a detecting portion of a concentration sensor and a detection principle according to the embodiment of the present invention.

Here, as shown in FIG. 2, the detecting portion 32B, temperature sensors A and B are disposed on two positions close to each other, and a heater is incorporated in the temperature sensor A. Then, when the heater incorporated in the temperature sensor A is operated for a predetermined period of time $t_1$, the temperature of the temperature sensor A itself rises, and also, the temperature of the temperature sensor B gradually rises with a characteristic according to the thermal conductivity of the urea aqueous solution. Therefore, immediately after the operation of the heater is stopped, the concentration of the urea aqueous solution is indirectly measured based on a difference between the temperatures detected by the temperature sensors A and B, that is, heat transfer characteristics using the urea aqueous solution as a thermal conducting medium. On the other hand, after the operation of the heater is stopped, the temperatures of the temperature sensors A and B are gradually lowered, and spend a time $t_2$ to return to the temperatures before the heater operation. Therefore, the concentration of the urea aqueous solution can be measured at each predetermined time $(t_1+t_2)$. Incidentally, FIG. 2 shows only a correlation between the temperatures detected by the temperature sensors A and B. As the concentration sensor 32, the one manufactured and distributed by Mitsui Mining and Smelting Co., Ltd. in Japan is known.

Figure 3:
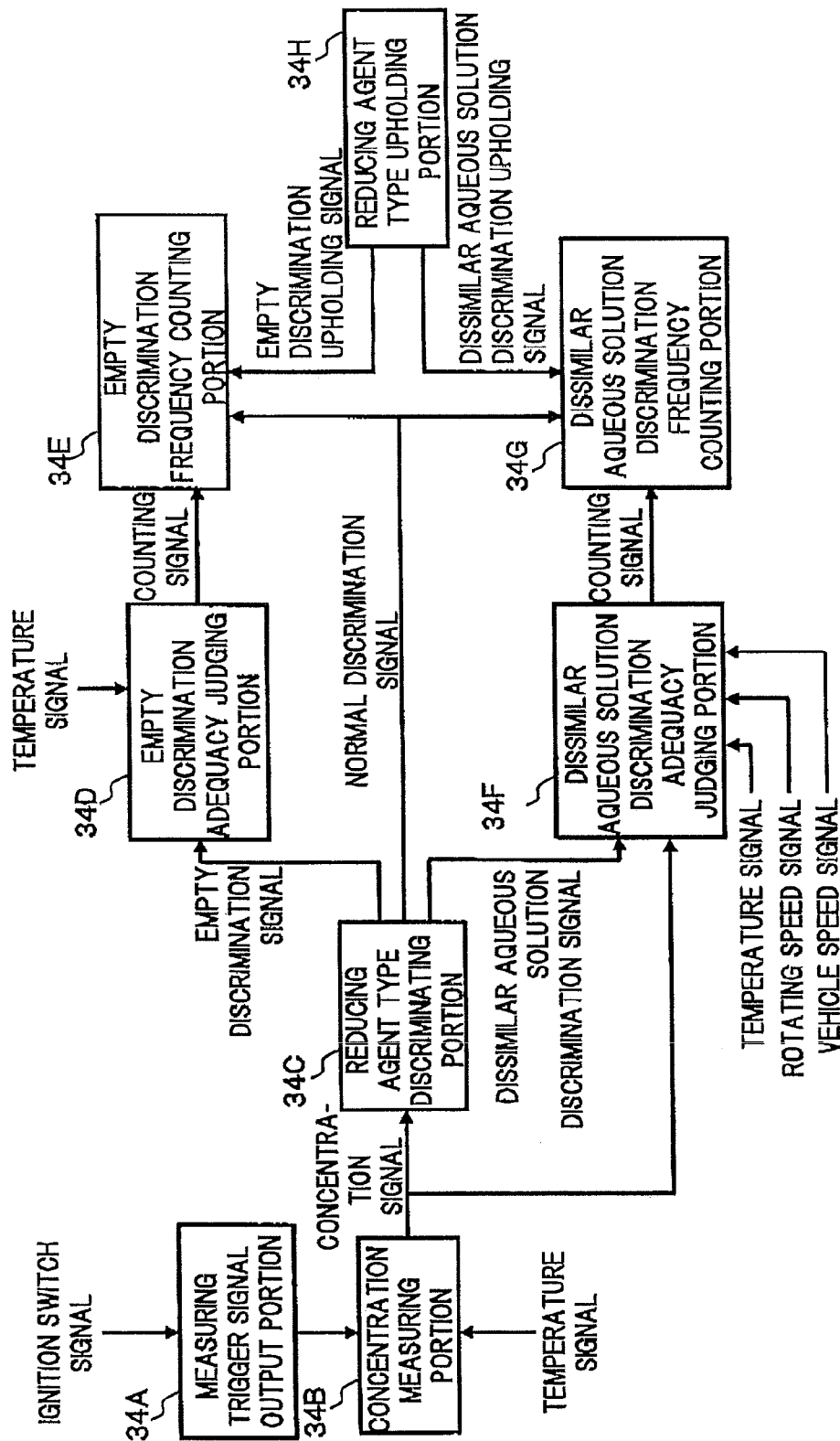
FIG. 3 is a block diagram of units exhibiting various functions, which configure the apparatus for discriminating liquid reducing agent according to the embodiment of the present invention.

An output signal from the concentration sensor 32, to be specific, temperature signals detected by the temperature sensors A and B, is input to a control unit 34 incorporating therein a computer. Further, the control unit 34 receives an engine rotating speed signal, an ignition switch signal, a vehicle speed signal and the like, from an engine control unit 36 which performs various controls of the engine 10, via CAN (Controller Area Network) and the like. Then, in the control unit 34, in accordance with a control program stored in a ROM (Read Only Memory) thereof, as shown in FIG. 3, there are realized a measuring trigger signal output portion 34A, a concentration measuring portion 34B, a reducing agent type discriminating portion 34C, an empty discrimination adequacy judging portion 34D, an empty discrimination frequency counting portion 34E, a dissimilar aqueous solution discrimination adequacy judging portion 34F, a dissimilar aqueous solution discrimination frequency counting portion 34G and a reducing agent type upholding portion 34H. In the present embodiment, the engine control unit 36 functions as a rotating speed sensor and also a vehicle speed sensor.

The measuring trigger signal output portion 34A is activated when the ignition switch signal is tuned ON, and outputs a measuring trigger signal indicating that the concentration of the urea aqueous solution is to be started measuring, at each predetermined time $(t_1+t_2)$ shown in FIG. 2. The concentration measuring portion 34B operates the heater in the concentration sensor 32 for the predetermined time $t_1$ when the measuring trigger signal is output, to indirectly measure the concentration of the urea aqueous solution based on the temperature signals from the concentration sensor 32. The reducing agent type discriminating portion 34C discriminates, based on the concentration measured by the concentration measuring portion 34B, whether the storage tank 18 is empty, the liquid reducing agent is normally filled or the liquid in the storage tank is the dissimilar aqueous solution, to output an empty discrimination signal, a normal discrimination signal or a dissimilar aqueous solution discrimination signal according to the discrimination result. The empty discrimination adequacy judging portion 34D judges, based on the temperature signals from the concentration sensor 32, whether or not the empty discrimination is adequate, when the empty discrimination signal is output, and also, outputs, if necessary, an empty discrimination frequency counting signal indicating that the empty discrimination frequency is required to be counted up. The empty discrimination frequency counting portion 34E counts up the empty discrimination frequency, when the empty discrimination frequency counting signal is output. The dissimilar aqueous solution discrimination adequacy judging portion 34F judges, based on the temperature signals, the concentration signal, the engine rotating speed signal and the vehicle speed signal, whether or not the dissimilar aqueous solution discrimination is adequate, when the dissimilar aqueous solution discrimination signal is output, and also, outputs, if necessary, a dissimilar aqueous solution discrimination frequency counting signal indicating that the dissimilar aqueous solution frequency is required to be counted up. The dissimilar aqueous solution frequency counting portion 34G counts up the dissimilar aqueous solution discrimination frequency, when the dissimilar aqueous solution discrimination frequency counting signal is output. The reducing agent type upholding portion 34H upholds the empty discrimination or the dissimilar aqueous solution discrimination when the empty discrimination frequency or the dissimilar aqueous solution discrimination frequency become equal to or larger than the first predetermined frequency, to output the empty discrimination upholding signal or the dissimilar aqueous solution discrimination upholding signal.

Next, there will be described various functions of the apparatus for discriminating liquid reducing agent, referring to the flowcharts of FIG. 4 through FIG. 11.

Figure 4:
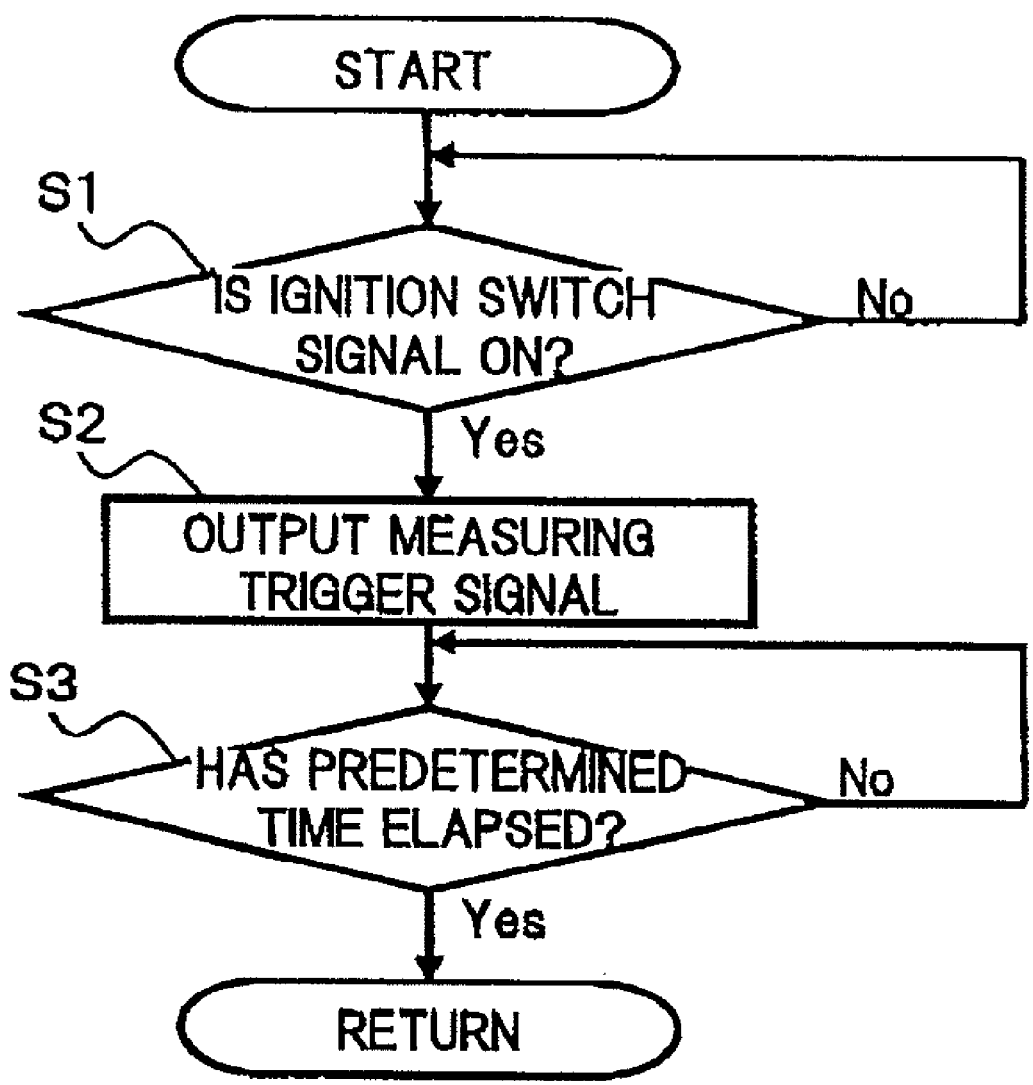
FIG. 4 is a flowchart showing measuring trigger signal output process according to the embodiment of the present invention.

In FIG. 4 showing the process for outputting a measuring trigger signal executed by the measuring trigger signal output portion 34A, in step 1 (to be abbreviated as S1 in the drawing, and the same rule will be applied to the subsequent steps), it is judged whether or not the ignition switch signal is ON, in other words, whether or not the engine 10 starts to be operated. Then, if the ignition switch signal is ON (Yes), the routine proceeds to step 2, whereas if the ignition switch signal is OFF (No), the routine is in a stand-by mode.

In step 2, the measuring trigger signal is outputted.

In step 3, it is judged whether or not the predetermined time $(t_1+t_2)$ has elapsed after the measuring trigger signal was output. Then, if the predetermined time $(t_1+t_2)$ has elapsed after the measuring trigger signal was output (Yes), the routine is terminated, whereas if the predetermined time $(t_1+t_2)$ has not elapsed (No), the routine is in the stand-by mode.

According to this measuring trigger signal output process, when the engine 10 starts to be operated, the measuring trigger signal is output at each predetermined time $(t_1+t_2)$. Therefore, it is possible to recognize whether or not the concentration of the urea aqueous solution is able to be measured by the concentration sensor 32, by monitoring whether or not the measuring trigger signal is output.

Figure 5:
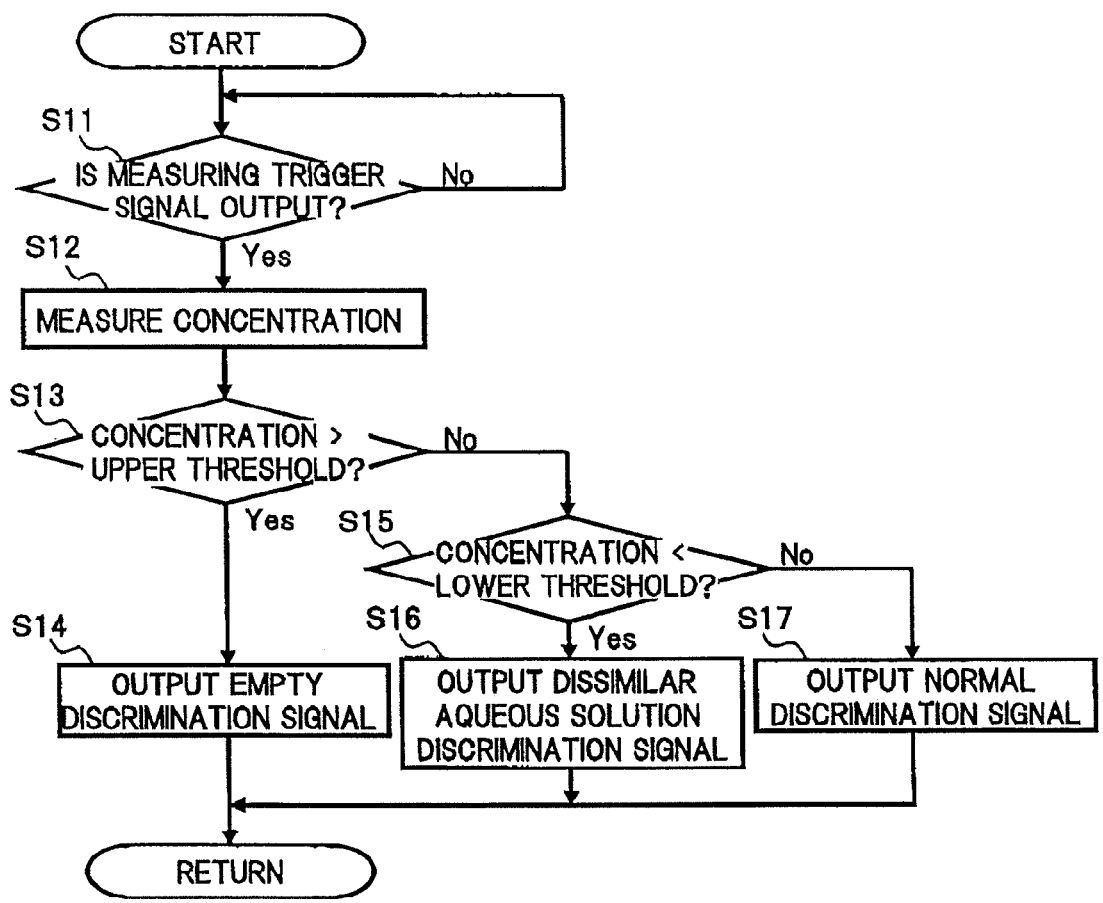
FIG. 5 is a flowchart showing concentration measuring process and reducing agent type discriminating process executed in the embodiment of the present invention.

In FIG. 5 showing the process of concentration measuring executed by the concentration measuring portion 34B and the process for discriminating a reducing agent type executed by the reducing agent type discriminating portion 34C, in step 11, it is judged whether or not the measuring trigger signal is output. Then, if the measuring trigger signal is output (Yes), the routine proceeds to step 12, whereas if the measuring trigger signal is not output (No), the routine is in the stand-by mode.

In step 12, the concentration of the urea aqueous solution is measured. Namely, the heater in the concentration sensor 32 is operated for the predetermined time $t_1$, so that the concentration of the urea aqueous solution is indirectly measured based on the difference between the temperatures detected by the temperature sensors A and B.

In step 13, it is judged whether or not the concentration of the urea aqueous solution is higher than an upper threshold. Here, the upper threshold is a threshold for discriminating whether or not the storage tank is empty, and is set at an upper limit value which is usually unable to be measured even if some convection is generated in the case where the urea aqueous solution is normally filled. Then, if the concentration of the urea aqueous solution is higher than the upper threshold (Yes), the routine proceeds to step 14 where the empty discrimination signal is output. On the other hand, if the concentration of the urea aqueous solution is equal to or lower than the upper threshold (No), the routine proceeds to step 15.

In step 15, it is judged whether or not the concentration of the urea aqueous solution is lower than a lower threshold. Here, the lower threshold is a threshold for discriminating whether or not the liquid in the storage tank is the dissimilar aqueous solution, and is set at a lower limit value which is usually unable to be measured even if some convection is generated in the case where the urea aqueous solution is normally filled. Then, if the concentration of the urea aqueous solution is lower than the lower threshold (Yes), the routine proceeds to step 16 where the dissimilar aqueous solution discrimination signal is output. On the other hand, if the concentration of the urea aqueous solution is equal to or higher than the lower threshold (No), the routine proceeds to step 17 where the normal discrimination signal is output.

According to the above-described concentration measuring process and reducing agent type discriminating process, the concentration of the urea aqueous solution is measured at each time when the measuring trigger signal is output. Then, if the concentration of the urea aqueous solution is higher than the upper threshold, it is discriminated that the storage tank is empty, and the empty discrimination signal indicating the discrimination result is output. If the concentration of the urea aqueous solution is lower than the lower threshold, it is discriminated that the liquid in the storage tank is the dissimilar aqueous solution, and the dissimilar aqueous solution discrimination signal indicating the discrimination result is output. On the other hand, if the concentration of the urea aqueous solution is equal to or higher than the lower threshold and also equal to or lower than the upper threshold, it is discriminated that the urea aqueous solution is normally filled in the storage tank and the normal discrimination signal indicating the discrimination result is outputted.

Figure 6:
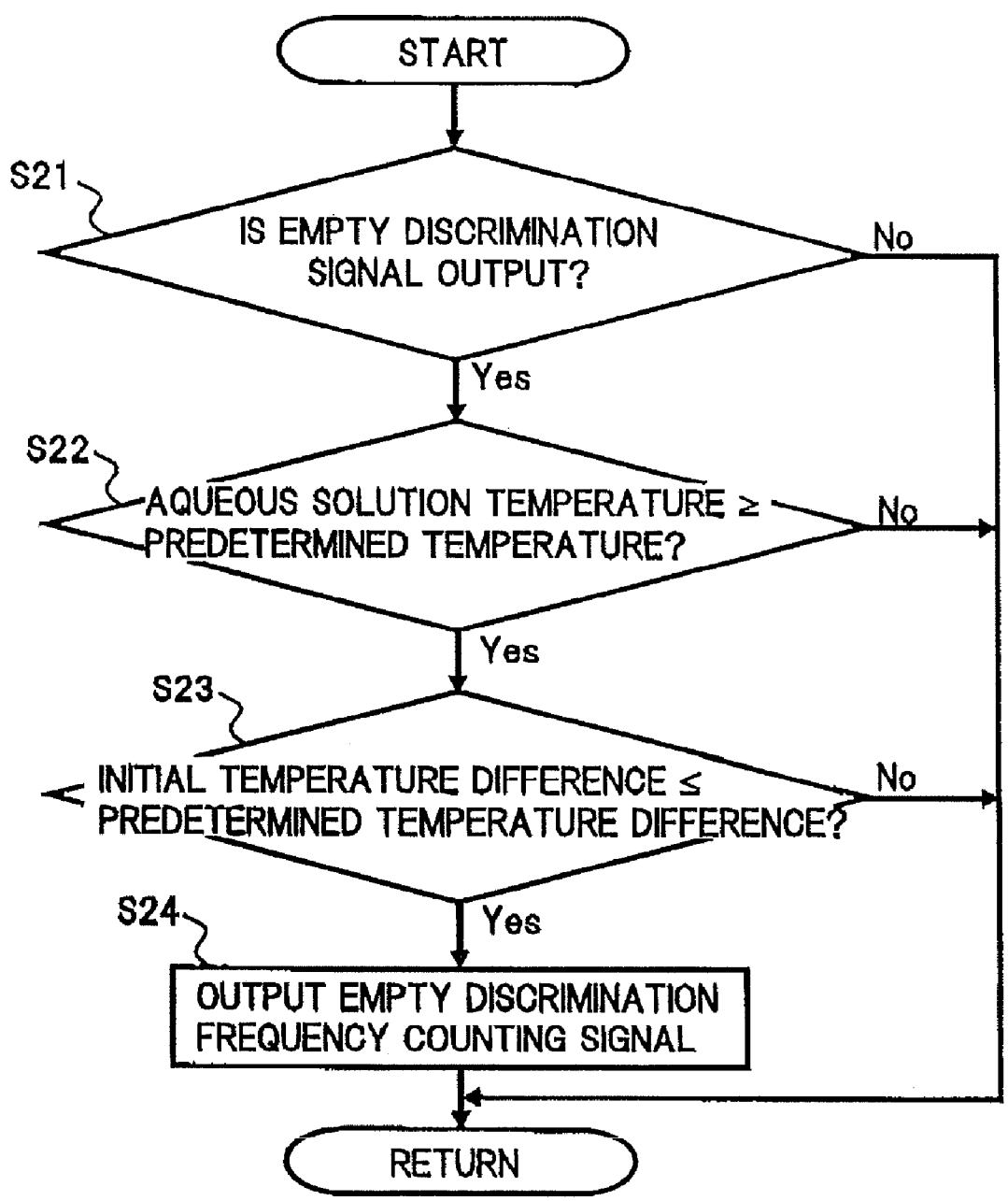
FIG. 6 is a flowchart showing empty discrimination adequacy judging process executed in the embodiment of the present invention.

In FIG. 6 showing the judging process of an empty discrimination adequacy executed by the empty discrimination adequacy judging portion 34D, in step 21, it is judged whether or not the empty discrimination signal is output. Then, if the empty discrimination signal is output (Yes), the routine proceeds to step 22, whereas if the empty discrimination signal is not output (No), the routine is terminated.

In step 22, it is judged whether or not the temperature of the urea aqueous solution is equal to or higher than the predetermined temperature, based on the temperature signals from the concentration sensor 32 immediately before the heater operation. Here, the predetermined temperature is a threshold based on which judgment is executed as to whether or not the concentration measuring precision is degraded as a result that at least a part of the urea aqueous solution is frozen, and is set at the temperature slightly higher than a freezing point of solvent of the urea aqueous solution. Then, if the temperature of the urea aqueous solution is equal to or higher than the predetermined temperature (Yes), the routine proceeds to step 23, whereas if the temperature of the urea aqueous solution is lower than the predetermined temperature (No), the routine is terminated.

In step 23, it is judged whether or not the difference between the temperatures detected by the temperature sensors A and B (to be referred to as "initial temperature difference" hereunder) is equal to or smaller than a predetermined temperature difference, based on the temperature signals from the concentration sensor 32 immediately before the heater operation. Here, the initial temperature difference is a threshold based on which judgment is executed as to whether or not the convection is generated in the urea aqueous solution, via the temperature difference between the two positions on which the temperature sensors A and B are disposed, and is set at a temperature difference which is usually unable to be resulted even if some convection is generated. Then, if the initial temperature difference is equal to or smaller than the predetermined temperature difference (Yes), the routine proceeds to step 24 where the empty discrimination frequency counting signal is output. On the other hand, if the initial temperature difference is larger than the predetermined temperature difference (No), the routine is terminated.

According to this empty discrimination adequacy judging process, when the empty discrimination signal is outputted, if the temperature of the urea aqueous solution is equal to or higher than the predetermined temperature and also the initial temperature difference is equal to or smaller than the predetermined temperature difference, it is judged that the empty discrimination is adequate, and the empty discrimination frequency counting signal is outputted. Therefore, in a state where the temperature of the urea aqueous solution is low and at least a part thereof is frozen, and in a state where strong convection is generated in the urea aqueous solution so that the heat transfer characteristics are changed, it is not judged that the empty discrimination is adequate, and accordingly, the high reliable empty discrimination can be performed.

Figure 7:
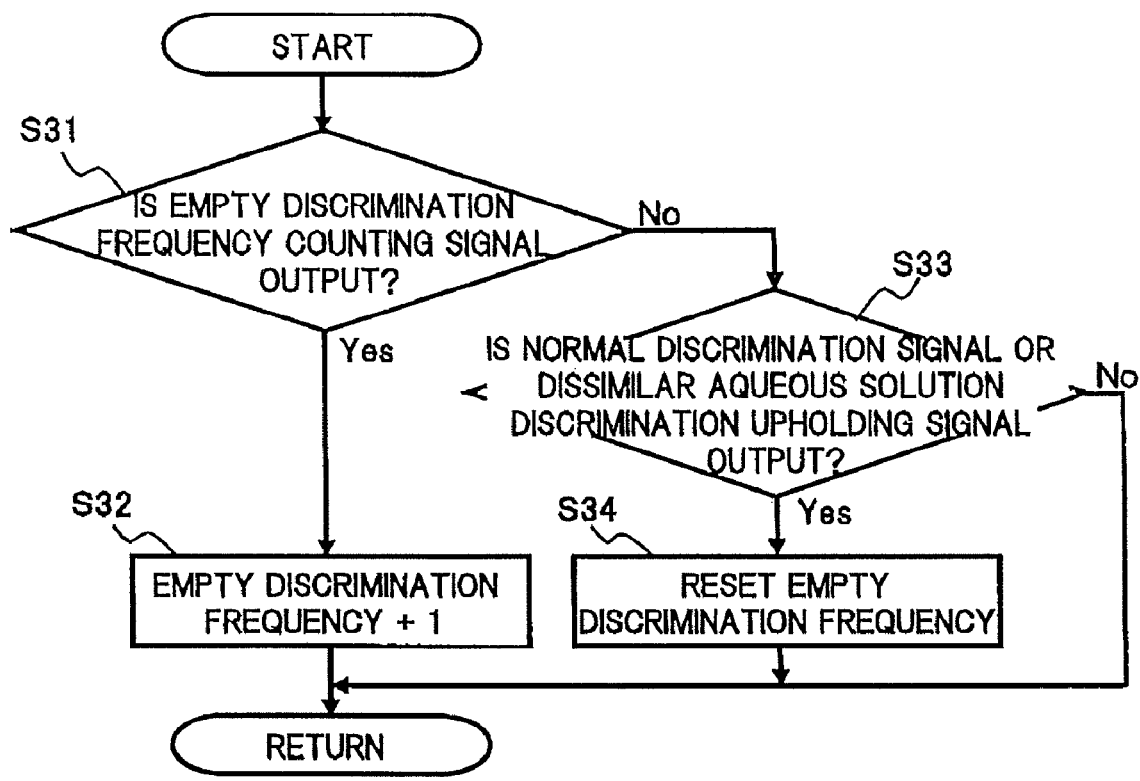
FIG. 7 is a flowchart showing empty discrimination frequency counting process executed in the embodiment of the present invention.

In FIG. 7 showing the process for counting an empty discrimination frequency, which is executed by the empty discrimination frequency counting portion 34E, in step 31, it is judged whether or not the empty discrimination frequency counting signal is outputted. Then, if the empty discrimination frequency counting signal is outputted (Yes), the routine proceeds to step 32 where 1 is added to the empty discrimination frequency. On the other hand, if the empty discrimination frequency counting signal is not outputted (No), the routine proceeds to step 33.

In step 33, it is judged whether or not the normal discrimination signal or the dissimilar aqueous solution discrimination signal is output. Then if the normal discrimination signal or the dissimilar aqueous solution discrimination signal is outputted (Yes), the routine proceeds to step 34 where the empty discrimination frequency is reset. On the other hand, if neither the normal discrimination signal nor the dissimilar aqueous solution discrimination signal is outputted (No), the routine is terminated.

According to this empty discrimination frequency counting process, 1 is added to the empty discrimination frequency at each time when the empty discrimination frequency-counting signal is outputted. On the other hand, when the normal discrimination signal or the dissimilar aqueous solution discrimination signal is outputted, since there is a high probability that the urea aqueous solution is normally filled or the liquid in the storage tank is the dissimilar aqueous solution, another counting process of the empty discrimination frequency is again executed from the beginning in order to prevent any occurrence of the erroneous upholding for the liquid reducing agent to the possible utmost, the empty discrimination frequency is reset.

Figure 8:
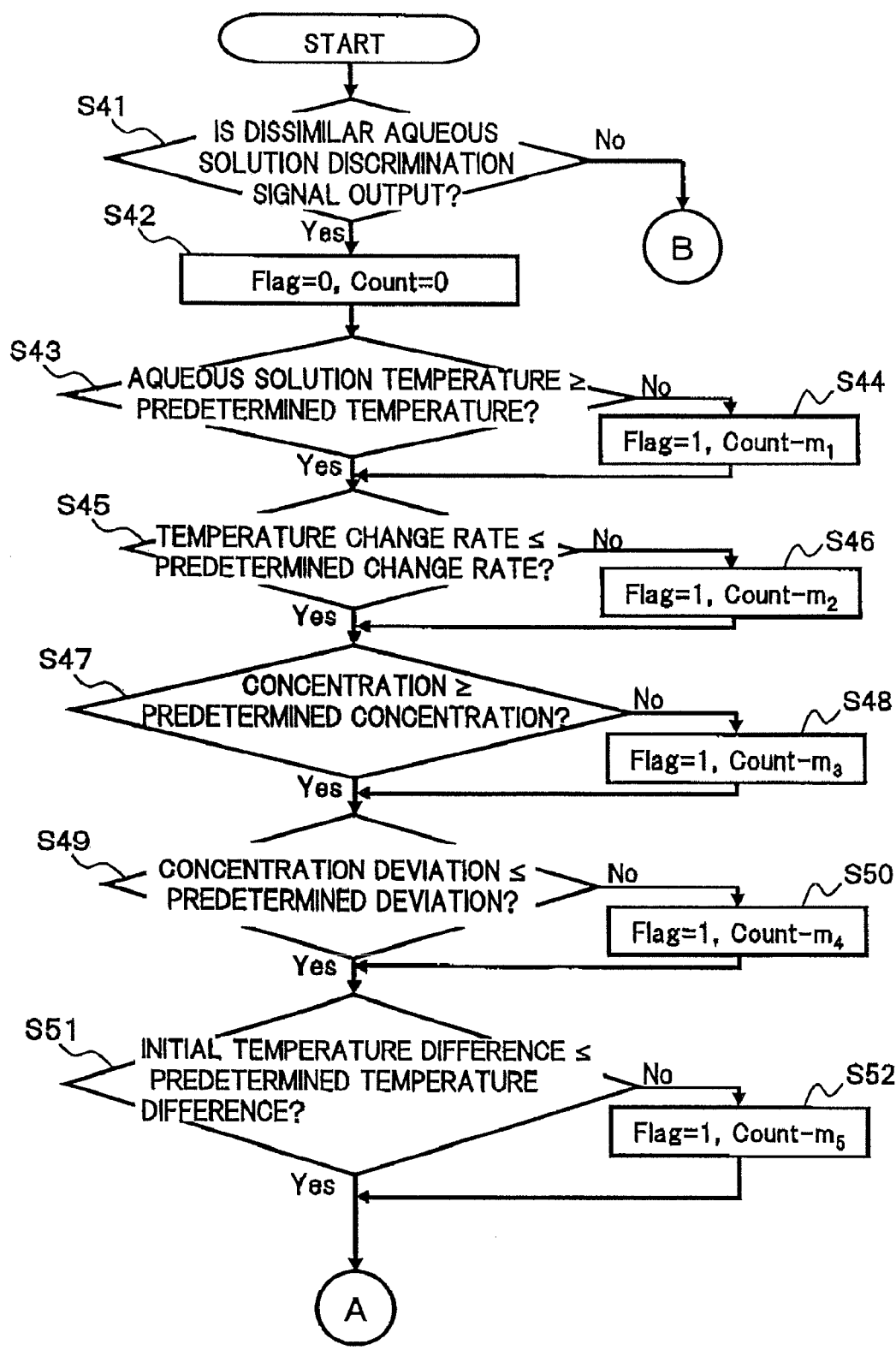
FIG. 8 is a flowchart showing dissimilar aqueous solution discrimination adequacy judging process executed in the embodiment of the present invention.
Figure 9:
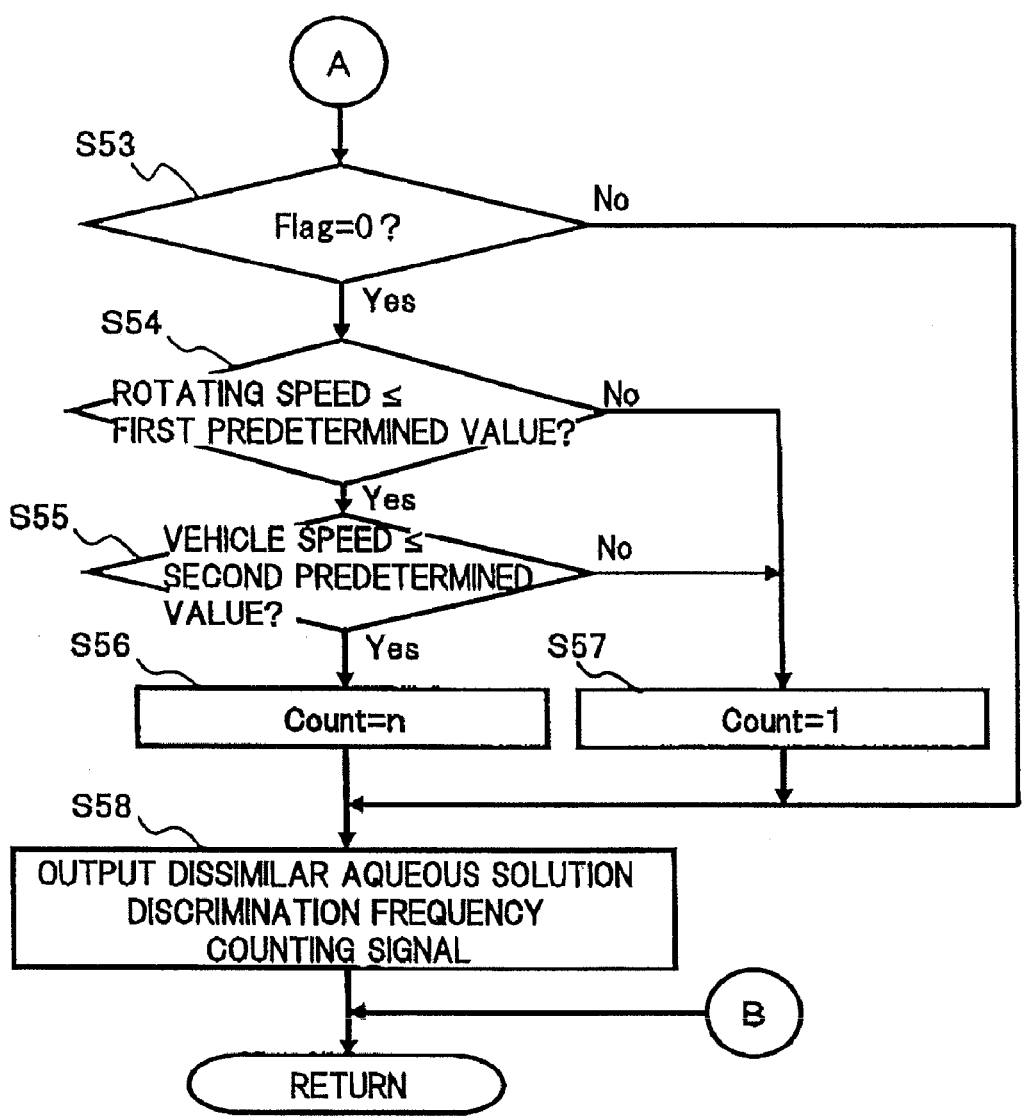
FIG. 9 is a flowchart showing dissimilar aqueous solution discrimination adequacy judging process executed in the embodiment of the present invention.

In FIG. 8 and FIG. 9 showing the judging process of dissimilar aqueous solution discrimination adequacy, which is executed by the dissimilar aqueous solution discrimination adequacy judging portion 34F, in step 41, it is judged whether or not the dissimilar aqueous solution discrimination signal is outputted. Then if the dissimilar aqueous solution discrimination signal is output (Yes), the routine proceeds to step 42, whereas if the dissimilar aqueous solution discrimination signal is not outputted (No), the routine is terminated.

In step 42, a flag "Flag" indicating whether or not the dissimilar discrimination is adequate is set at 0 (adequacy), and also, a variable "Count" indicating the counting frequency of the dissimilar aqueous solution discrimination frequency is set at 0. Here, as the variable "Count", a positive value is set when the dissimilar aqueous solution discrimination frequency is added, whereas a negative value is set when the dissimilar aqueous solution discrimination frequency is subtracted.

In step 43, it is judged whether or not the temperature of the urea aqueous solution is equal to or higher than the predetermined temperature, based on the temperature signals from the concentration sensor 32. Then, if the temperature of the urea aqueous solution is equal to or higher than the predetermined temperature (Yes), the routine proceeds to step 45. On the other hand, if the temperature of the urea aqueous solution is lower than the predetermined temperature (No), the routine proceeds to step 44 where the flag "Flag" is set at 1 (inadequacy) and also a predetermined value $m_1$ is subtracted from the variable "Count".

In step 45, it is judged whether or not a temperature change rate of the urea aqueous solution due to the heater operation, that is, a temperature change per unit time, is equal to or lower than a predetermined change rate, based on the temperature signal from the concentration sensor 32. Here, the predetermined change rate is a threshold based on which judgment is executed as to whether or not strong convection is generated, via the temperature change of the urea aqueous solution, and is set at a change rate which is usually unable to be adopted in a state where the convection is relatively weak. Then, if the temperature change rate of the urea aqueous solution is equal to or lower than the predetermined change rate (Yes), the routine proceeds to step 47. On the other hand, if the temperature change rate of the urea aqueous solution is higher than the predetermined change rate (No), the routine proceeds to step 46 where the flag "Flag" is set at 1 and also a predetermined value $m_2$ is subtracted from the variable "Count".

In step 47, it is judged whether or not the concentration of the urea aqueous solution is equal to or higher than the predetermined concentration, based on the concentration signal. Here, the predetermined concentration is a threshold based on which judgment is executed as to whether or not strong convection is generated in the urea aqueous solution, via a fact that the concentration measured based on the temperature signals from the concentration sensor 32 is significantly low, and is set at the low concentration which is unable to be measured even if some convection is generated. Then, if the concentration of the urea aqueous solution is equal to or higher than the predetermined concentration (Yes), the routine proceeds to step 49. On the other hand, if the concentration of the urea aqueous solution is lower than the predetermined concentration (No), the routine proceeds to step 48 where the flag "Flag" is set at 1 and also a predetermined value $m_3$ is subtracted from the variable "Count".

In step 49, it is judged whether or not the deviation between the previously measured urea aqueous solution concentration and the presently measured urea aqueous solution concentration (to be referred to as the concentration deviation) is equal to or smaller than the predetermined deviation. Here, the predetermined deviation is a threshold based on which judgment is executed as to whether or not strong convection is generated in the urea aqueous solution, via a fact such that the concentration of the urea aqueous solution is significantly changed, and is set at the deviation within a range where the deviation is not changed even if some convection is generated. Then, if the concentration deviation is equal to or smaller than the predetermined deviation (Yes), the routine proceeds to step 51. On the other hand, if the concentration deviation is larger than the predetermined deviation (No), the routine proceeds to step 50 where the flag "Flag" is set at 1 and also, a predetermine value $m_4$ is subtracted from the variable "Count".

In step 51, it is judged whether or not the initial temperature difference is equal to or smaller than the predetermined temperature difference. Then, if the initial temperature difference is equal to or smaller than the predetermined temperature difference (Yes), the routine proceeds to step 53. On the other hand, if the initial temperature difference is larger than the predetermined temperature difference (No), the routine proceeds to step 52 where the flag "Flag" is set at 1 and also a predetermined value $m_5$ is subtracted from the variable "Count".

In step 53, it is judged whether or not the flag "Flag" is 0, namely, whether or not the dissimilar aqueous solution discrimination is adequate. Then, if the flag "Flag" is 0 (Yes), the routine proceeds to step 54, whereas if the flag "Flag" is 1 (No), the routine proceeds to step 58.

In step 54, it is judged whether or not the engine rotating speed is equal to or smaller than a first predetermined value. Here, the first predetermined value is one of thresholds based on which judgment is executed as to whether or not the vehicle is in a stop state, and is appropriately set according to the detecting precision of the engine rotating speed. Then, if the engine rotating speed is equal to or smaller than the first predetermined value (Yes), the routine proceeds to step 55, whereas if the engine rotating speed is larger than the first predetermined value (No), the routine proceeds to step 57.

In step 55, it is judged whether or not the vehicle speed is equal to or smaller than a second predetermined value. Here, the second predetermined value is the other threshold based on which judgment is executed as to whether or not the vehicle is in the stop state, and is appropriately set according to the detecting precision of the vehicle speed. Then, if the vehicle speed is equal to or smaller than the second predetermined value (Yes), the routine proceeds to step 56, whereas if the vehicle speed is larger than the second predetermined value (No), the routine proceeds to step 57.

In step 56, it is judged that the vehicle is in the stop state, and natural number n equal to or larger than 2 is set to the variable "Count".

In step 57, it is judged that the vehicle is in a running state, and 1 is set to the variable "Count".

In step 58, the dissimilar aqueous solution discrimination frequency counting signal inclusive of the counting frequency set to the variable "Count" is outputted.

According to this dissimilar aqueous solution discrimination adequacy judging process, when the dissimilar aqueous solution discrimination signal is outputted, it is judged that the dissimilar aqueous solution discrimination is adequate if the following conditions are satisfied; the temperature of the urea aqueous solution is equal to or higher than the predetermined temperature; the temperature change rate of the urea aqueous solution is equal to or lower than the predetermined change rate; the concentration of the urea aqueous solution is equal to or higher than the predetermined concentration; the concentration deviation is equal to or smaller than the predetermined deviation; and the initial temperature difference is equal to or smaller than the predetermined temperature difference. Therefore, in the state where the temperature of the urea aqueous solution is low and at least a part thereof is frozen, and in the state where strong convection is generated in the urea aqueous solution so that the heat transfer characteristics are changed, it is not judged that the dissimilar aqueous solution discrimination is adequate, and therefore, the high reliable dissimilar aqueous solution discrimination can be performed. At this time, it is judged whether the vehicle is in the stop state or in the running state, based on the engine rotating speed and the vehicle speed. If the vehicle is in the stop state, in order to enable in a short time to uphold that the liquid in the storage tank is the dissimilar aqueous solution, the dissimilar aqueous solution discrimination frequency counting signal in which natural number n equal to or larger than 2 is set as the counting frequency is outputted. On the other hand, if the vehicle is in the running state, the dissimilar aqueous solution discrimination frequency counting signal in which 1 is set as the counting frequency is outputted.

On the other hand, it is judged that the dissimilar aqueous solution discrimination is performed in the state where strong convection is generated in the urea aqueous solution if the following conditions are satisfied: the temperature of the urea aqueous solution is lower than the predetermined temperature; the temperature change rate of the urea aqueous solution is higher than the predetermined change rate; the concentration of the urea aqueous solution is lower than the predetermined concentration; the concentration deviation is larger than the predetermined deviation; and the initial temperature difference is larger than the predetermined temperature difference. Thereafter, in order to cancel the dissimilar aqueous solution discrimination frequency, the dissimilar aqueous solution discrimination frequency counting signal in which the negative value is set as the counting frequency is output. At this time, although natural numbers $m_1$ through $m_5$ are subtracted as the counting frequency in steps 44, 46, 48, 50 and 52, respectively, in the case where the subtractive condition is not used, 0 may be appropriately set to respective natural numbers $m_1$ through $m_5$. Incidentally, when 0 is set to all of natural numbers $m_1$ through $m_5$, it is possible to maintain the counting frequency without the necessity of subtracting the dissimilar aqueous solution discrimination frequency.

Figure 10:
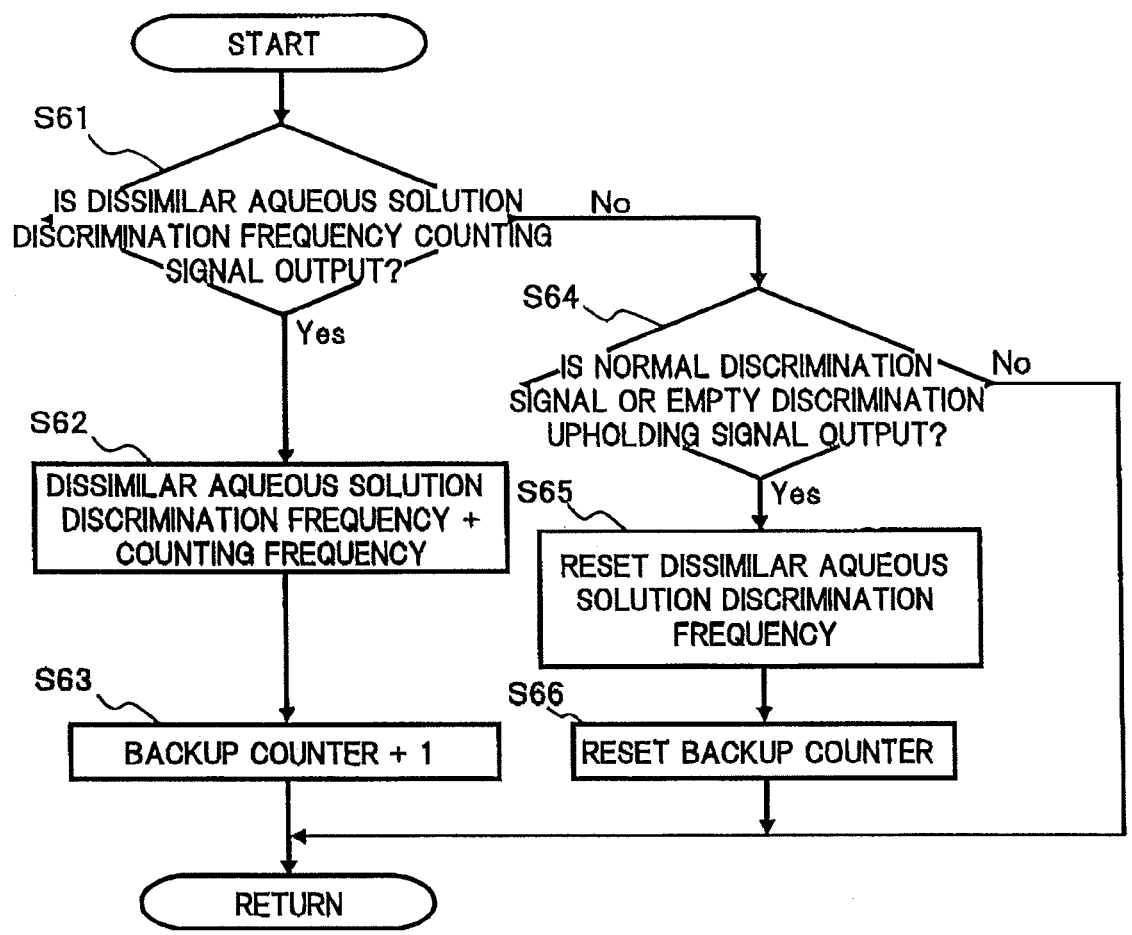
FIG. 10 is a flowchart showing dissimilar aqueous solution discrimination frequency counting process executed in the embodiment of the present invention.

In FIG. 10 showing dissimilar aqueous solution discrimination frequency counting process by the dissimilar aqueous solution discrimination frequency counting portion 34G, in step 61, it is judged whether or not the dissimilar aqueous solution discrimination frequency counting signal is output. Then, if the dissimilar aqueous solution discrimination frequency counting signal is outputted (Yes), the routine proceeds to step 62, whereas if the dissimilar aqueous solution discrimination frequency counting signal is not outputted (No), the routine proceeds to step 64.

In step 62, the dissimilar aqueous solution discrimination frequency is counted up. Namely, when the dissimilar aqueous solution discrimination is adequate, the dissimilar aqueous solution discrimination frequency is added according to the counting frequency of positive integer included in the dissimilar aqueous solution discrimination frequency counting signal. On the other hand, when the dissimilar aqueous solution discrimination is inadequate, in order to cancel the counting in the inadequate state, the dissimilar aqueous solution discrimination frequency is subtracted according to the counting frequency of negative integer included in the dissimilar aqueous solution discrimination frequency counting signal.

In step 63, 1 is added to a backup counter indicating the frequency of consecutively performed dissimilar aqueous solution discrimination.

In step 54, it is judged whether or not the normal discrimination signal or the empty discrimination upholding signal is outputted. Then, if the normal discrimination signal or the empty discrimination upholding signal is outputted (Yes), the routine proceeds to step 65, whereas if neither the normal discrimination signal nor the empty discrimination upholding signal is output (No), the routine is terminated.

In step 65, the dissimilar aqueous solution discrimination frequency is reset.

In step 66, the backup counter is reset.

According to this dissimilar aqueous solution discrimination frequency counting process, the dissimilar aqueous solution discrimination frequency is counted up at each time when the dissimilar aqueous solution discrimination frequency counting signal is outputted. At this time, if the dissimilar aqueous solution discrimination is adequate, since the dissimilar aqueous solution discrimination frequency is added according to different counting frequency depending on the vehicle state (the stop state or the running state), in particular, it is possible to improve the counting speed in the stop state where the convection in the urea aqueous solution is weak. Further, if the dissimilar aqueous solution discrimination is inadequate, since the dissimilar aqueous solution discrimination frequency is subtracted in order to cancel the counting in the state where the convection in the urea aqueous solution is strong, in short, the counting in the state where the liquid type discrimination is hard to be performed, it is possible to improve the discriminating precision. Furthermore, 1 is added to the backup counter at each time when the dissimilar aqueous solution discrimination frequency counting signal is output, irrespectively of the dissimilar aqueous solution discrimination adequacy.

On the other hand, when the normal discrimination signal or the empty discrimination upholding signal is outputted, since there is a high probability that the urea aqueous solution is normally filled or the storage tank is empty, another counting process of the dissimilar aqueous solution discrimination frequency is again executed from the beginning in order to prevent an erroneous upholding for the liquid reducing agent to the possible utmost, the dissimilar aqueous solution discrimination frequency and the backup counter are reset.

Figure 11:
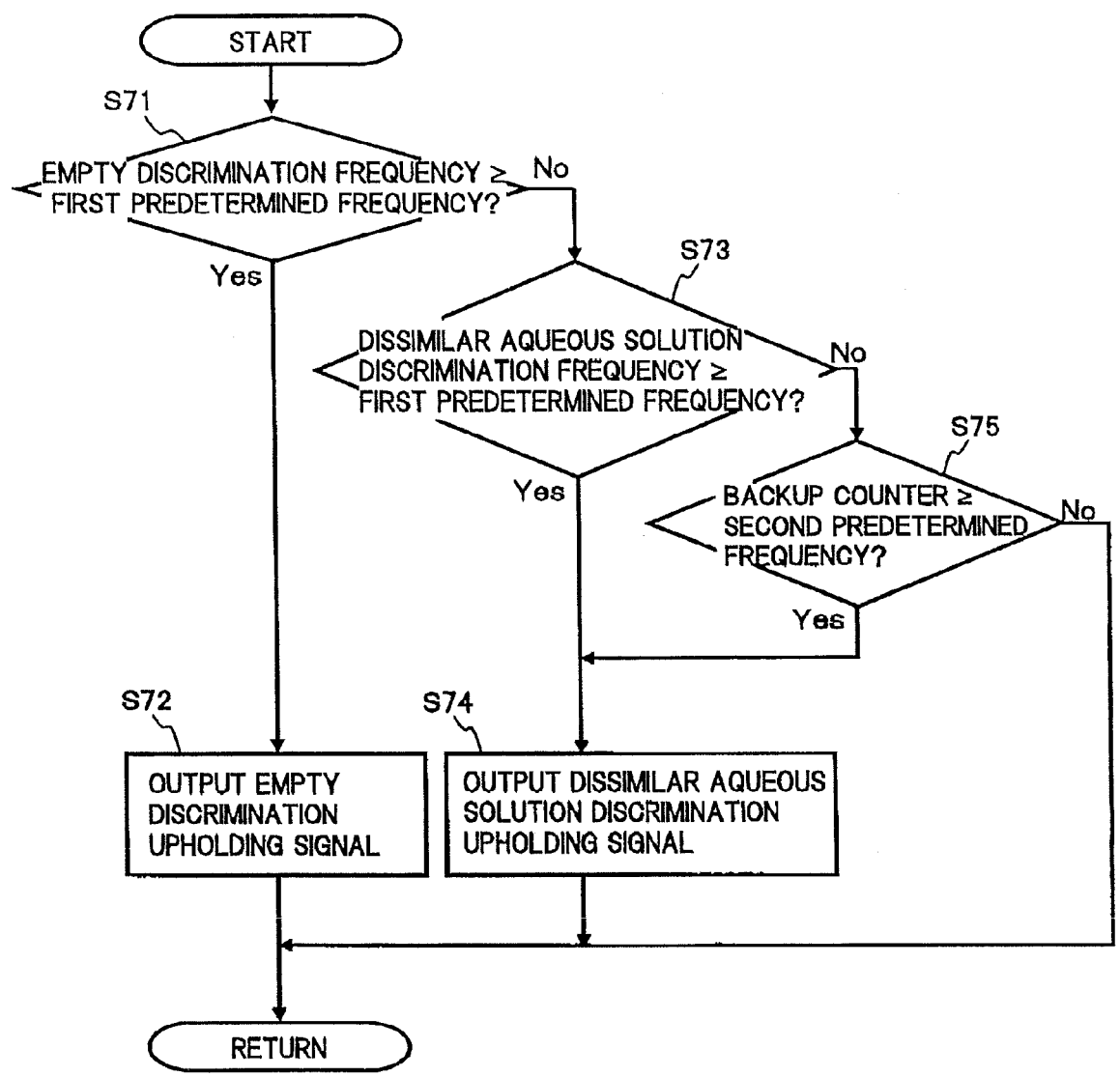
FIG. 11 is a flowchart showing reducing agent type upholding process.

In FIG. 11 showing reducing agent type upholding process by the reducing agent type upholding portion 34H, in step 71, it is judged whether or not the empty discrimination frequency is equal to or more than the first predetermined frequency. Then, if the empty discrimination frequency is equal to or more than the first predetermined frequency (Yes), the routine proceeds to step 72 where the empty discrimination upholding signal indicating that the empty discrimination is upheld is output. On the other hand, if the empty discrimination frequency is less than the first predetermined frequency (No), the routine proceeds to step 73.

In step 73, it is judged whether or not the dissimilar aqueous solution discrimination frequency is equal to or more than first predetermined frequency. Then, if the dissimilar aqueous solution discrimination frequency is equal to or more than the first predetermined frequency (Yes), the routine proceeds to step 74 where the dissimilar aqueous solution discrimination upholding signal indicating that the dissimilar aqueous solution discrimination is upheld is outputted. On the other hand, if the dissimilar aqueous solution discrimination frequency is less than the first predetermined frequency (No), the routine proceeds to step 75.

In step 75, it is judged whether or not the backup counter is equal to or more than second predetermined frequency. Here, the second predetermined frequency is a threshold for use in prohibiting occurrence of a state where the dissimilar aqueous solution discrimination is left aside without being implemented for a long time, and is set at a value larger than the first predetermined frequency, for example a value of ten times of the first predetermined frequency. Then, if the backup counter is equal to or more than the second predetermined frequency (Yes), the routine proceeds to step 74 where the dissimilar aqueous solution discrimination upholding signal is output. On the other hand, if the backup counter is less than the second predetermined frequency (No), the routine is terminated.

According to this reducing agent type upholding process, when the empty discrimination frequency or the dissimilar aqueous solution discrimination frequency becomes equal to or more than the first predetermined frequency, the empty discrimination or the dissimilar aqueous solution discrimination is upheld, so that the signal according to the upholding result is outputted. Further, when the backup counter indicating the frequency of consecutively performed dissimilar aqueous solution discrimination becomes equal to or more than the second predetermined frequency regardless of whether or not the dissimilar aqueous solution discrimination is adequate, the dissimilar aqueous solution discrimination is upheld, so that the dissimilar aqueous solution discrimination upholding signal is outputted.

Figure 12:
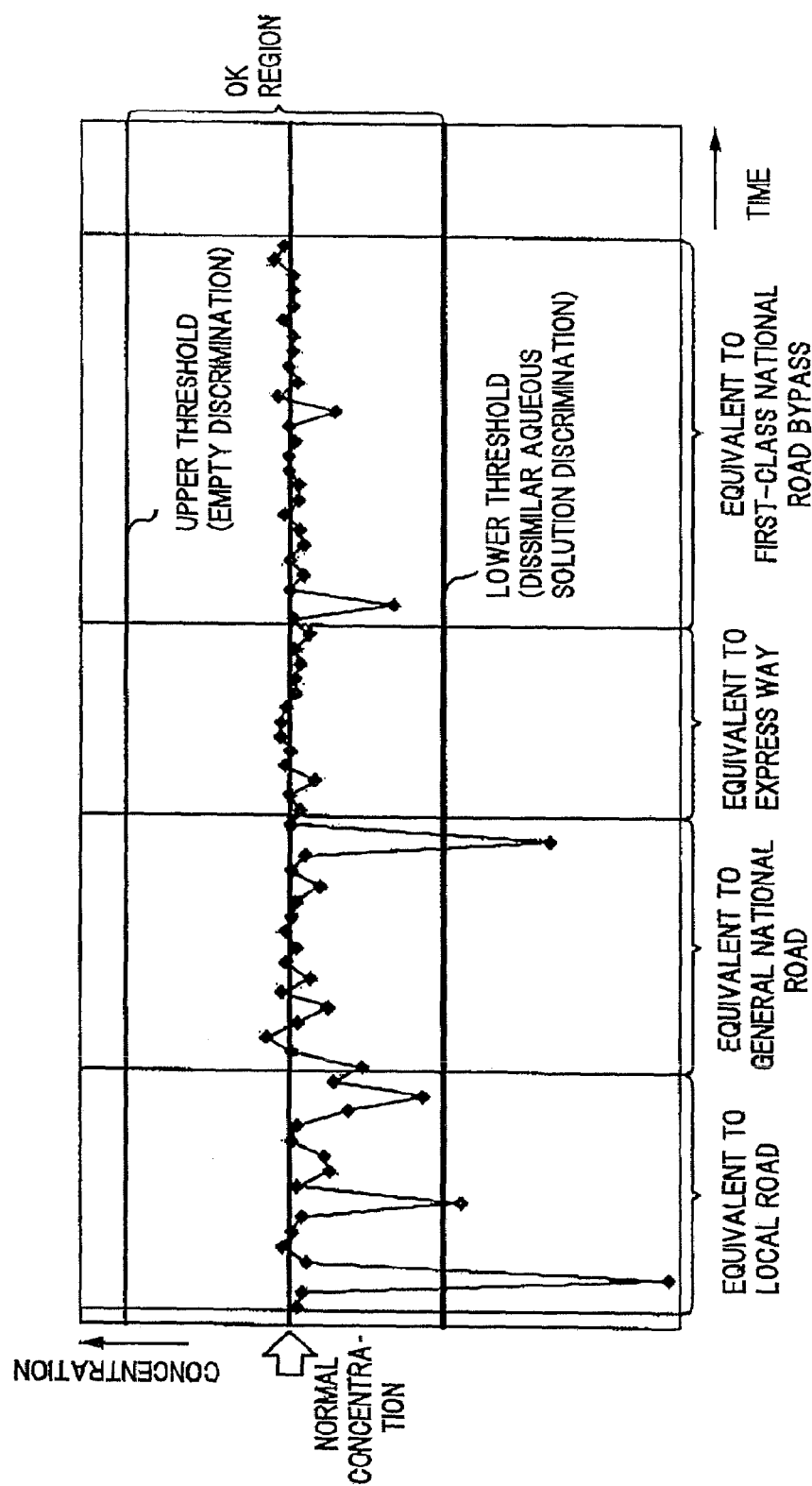
FIG. 12 is a characteristic diagram showing a measurement value of the concentration during the vehicle running.

Namely, if the convection is generated in the urea aqueous solution, since the heat generated by the heater incorporated in the temperature sensor A of the concentration sensor 32 is carried on the convection, a heat quantity to be transferred to the temperature sensor B is decreased so that the concentration measuring precision is degraded. However, according to the practical measurement of the concentration of the urea aqueous solution measured by the concentration sensor 32, as shown in FIG. 12, it could be found out that, if the urea aqueous solution is normally filled, it is extremely rare that the concentration is deviated from a predetermined range consecutively for many times even if the convection is generated.

Therefore, when the concentration of the urea aqueous solution becomes larger than the upper threshold or smaller than the lower threshold, it is discriminated that the storage tank is empty or the liquid in the storage tank is the dissimilar aqueous solution, and the discrimination frequency is individually counted up, and also, the discrimination is upheld when the discrimination frequency becomes equal to or more than the first predetermined frequency, so that the discrimination can be performed irrespectively of the vehicle states. At this time, the adequacy of the empty discrimination or of the dissimilar aqueous solution discrimination is judged and the discrimination frequency is counted up only when the empty discrimination or the dissimilar aqueous solution discrimination is adequate, so that the counting in the state where strong convection is generated in the urea aqueous solution can be prevented, thereby enabling the improvement of the discriminating precision.

Incidentally, in the dissimilar aqueous solution discrimination adequacy judging process shown in FIG. 8 and FIG. 9, in order to simplify the control program, 1 may be uniformly set as the counting frequency of the dissimilar aqueous solution discrimination frequency without taking the vehicle states into consideration.

Further, in the reducing agent type upholding process shown in FIG. 11, when the empty discrimination or the dissimilar aqueous solution discrimination is upheld, this upholding result may be noticed to a vehicle driver using an alarm device such as a warning device. Thus, since the vehicle driver can recognize at an early stage that the urea aqueous solution is not normally filled, the function as the exhaust emission purifying apparatus can be maintained by taking an appropriate action, such as the exchange and the like.

Furthermore, the configuration may be such that each of the dissimilar aqueous solution discrimination frequency and the empty discrimination frequency is written in a EEPROM (Electrically Erasable Programmable Read Only Memory) as a nonvolatile memory when the operation of the engine 10 is stopped, whereas each of the dissimilar aqueous solution discrimination frequency and the empty discrimination frequency written in the EEPROM is read out when the operation of the engine 10 is started. Thus, since the dissimilar aqueous solution discrimination frequency and the empty discrimination frequency before the operation start of the engine 10 are taken over to the next operation start of the engine 10, it is unnecessary to perform the counting process from the beginning at each time when the operation of the engine 10 is started, and accordingly, the discrimination of the urea aqueous solution can be performed in a short time.

Consequently, according to the apparatus for discriminating liquid reducing agent of the present invention, it is possible to discriminate with high precision whether the storage tank is empty, the liquid reducing agent is normally filled or the liquid in the storage tank is the dissimilar aqueous solution, in the case where the concentration sensor which indirectly measures the concentration of the liquid reducing agent based on the heat transfer characteristics between two positions close to each other is mounted on the moving vehicle.

It should be appreciated that the entire contents of Japanese Patent Application No. 2005-171391, filed on Jun. 10, 2005, on which the convention priority is claimed is incorporated herein by reference.

It should also be understood that many modifications and variations of the described embodiment of the invention will occur to a person having an ordinary skill in the art without departing from the spirit and scope of the present invention as claimed in the appended claims.

We claim:

1. An apparatus for discriminating liquid reducing agent, comprising:
   a concentration sensor that incorporates therein temperature sensors arranged at two positions close to each other in a storage tank storing a liquid reducing agent and a heater incorporated in one of the temperature sensors; and
   a control unit incorporating therein a computer,
   wherein the control unit:
   operates the heater of the concentration sensor at each predetermined time after a start of an engine operation to thereby indirectly measure a concentration of the liquid reducing agent based on a temperature detected by each of the temperature sensors;
   processes discrimination in a manner such that the storage tank is filled with a dissimilar aqueous solution that is dissimilar from the liquid reducing agent when the concentration is lower than a lower threshold, that the storage tank is normally filled with the liquid reducing agent when the concentration is equal to or higher than the lower threshold and also equal to or lower than an upper threshold, and that the storage tank is empty when the concentration is higher than the upper threshold;
   judges, upon discrimination of the storage tank being filled with the dissimilar aqueous solution, whether or not a dissimilar aqueous solution discrimination is adequate, based on the temperature detected by each of the temperature sensors and the concentration measured by the concentration sensor, and counts up, upon being judged that the dissimilar aqueous solution discrimination is adequate, a frequency of the dissimilar aqueous solution discrimination;
   judges, upon discrimination of the storage tank being empty, whether or not an empty discrimination is adequate, based on the temperature detected by each of the temperature sensors, and counts up, upon being judged that the empty discrimination is adequate, a frequency of the empty discrimination;
   resets, upon discrimination of the storage tank being normally filled, the frequency of the dissimilar aqueous solution discrimination and the frequency of the empty discrimination; and
   upholds the dissimilar aqueous solution discrimination and the empty discrimination when the frequency of the dissimilar aqueous solution discrimination and the frequency of the empty discrimination become equal to or larger than a first predetermined frequency.

2. The apparatus according to claim 1, wherein the control unit judges that the dissimilar aqueous solution discrimination is adequate, when a temperature, which is based on the temperature detected by each of the temperature sensors, immediately before a heater operation is equal to or higher than a predetermined temperature, a temperature difference immediately before the heater operation is equal to or smaller than a predetermined temperature difference, a change rate of the temperature caused by the heater operation is equal to or lower than a predetermined change rate, the concentration is equal to or higher than the predetermined concentration which is lower than the lower threshold, and a deviation between a previously measured concentration and the currently measured concentration is equal to or smaller than a predetermined deviation.

3. The apparatus according to claim 1, wherein the control unit judges that the empty discrimination is adequate, when a temperature, which is based on the temperature detected by each of the temperature sensors, immediately before a heater operation is equal to or higher than a predetermined temperature and a temperature difference immediately before the heater operation is equal to or smaller than a predetermined temperature difference.

4. The apparatus according to claim 1, wherein the control unit resets the frequency of the dissimilar aqueous solution discrimination when the empty discrimination is upheld, and also, resets the frequency of the empty discrimination when the dissimilar aqueous solution discrimination is upheld.

5. The apparatus according to claim 1, wherein the control unit upholds the dissimilar aqueous solution discrimination, when the frequency of consecutively performed discrimination that the liquid in the storage tank is the dissimilar aqueous solution becomes equal to or larger than a second predetermined frequency which is larger than the first predetermined frequency, regardless of whether or not the frequency of the dissimilar aqueous solution discrimination becomes equal to or larger than the first predetermined frequency.

6. The apparatus according to claim 1, wherein the control unit subtracts a predetermined frequency from the frequency of the dissimilar aqueous solution discrimination when it is judged that the dissimilar aqueous solution discrimination is inadequate.

7. The apparatus according to claim 1, wherein the control unit is further configured to write, in a nonvolatile memory incorporated therein, the frequency of the dissimilar aqueous solution discrimination and the frequency of the empty discrimination when the engine operation is stopped, and also, reads out of the memory the frequency of the dissimilar aqueous solution discrimination and the frequency of the empty discrimination when the engine operation is started.

8. The apparatus according to claim 1, wherein when the empty discrimination or the dissimilar aqueous solution discrimination is upheld, the control unit notifies upholding of the empty or the dissimilar aqueous solution discrimination via an alarm device.

9. The apparatus according to claim 1, wherein the control unit judges whether a vehicle is in a running state or a stop state, and when it is judged that the vehicle is in the stop state, adds natural number equal to or larger than 2 to the frequency of the dissimilar aqueous solution discrimination.

10. The apparatus according to claim 9, further comprising: a rotating speed sensor that detects a rotating speed of the engine; and a vehicle speed sensor that detects the vehicle speed, wherein the control unit:
    judges that the vehicle is in the stop state under a condition where the rotating speed detected by the rotating speed sensor is equal to or lower than a first predetermined value and also the vehicle speed detected by the vehicle speed sensor is equal to or lower than a second predetermined value; but
    judges that the vehicle is in the running state under another condition except for the above-mentioned condition.

* * * * *

UNITED STATES PATENT AND TRADEMARK OFFICE
CERTIFICATE OF CORRECTION

| | | |
|---|---|---|
| PATENT NO. | : 7,651,262 B2 | Page 1 of 1 |
| APPLICATION NO. | : 11/945201 | |
| DATED | : January 26, 2010 | |
| INVENTOR(S) | : Mitsuhiro Nishina et al. | |

It is certified that error appears in the above-identified patent and that said Letters Patent is hereby corrected as shown below:

ON THE COVER:
    (30) Foreign Application Priority Data: Replace "Oct. 6, 2005" with --Jun. 10, 2005--.

On Column 11, Line 53: Replace "54" with --64--.

Signed and Sealed this

Thirteenth Day of July, 2010

David J. Kappos
*Director of the United States Patent and Trademark Office*